(12) United States Patent
Gavrielov et al.

(10) Patent No.: US 10,492,528 B2
(45) Date of Patent: Dec. 3, 2019

(54) POWER SUPPLY SECTION CONFIGURATION FOR AN ELECTRONIC VAPING DEVICE AND ELECTRONIC VAPING DEVICE

(71) Applicant: Altria Client Services LLC, Richmond, VA (US)

(72) Inventors: Shmuel Gavrielov, Beit Shemesh (IL); Moshe Eliyahu, Beit Shemesh (IL)

(73) Assignee: Altria Client Services LLC, Richmond, VA (US)

( * ) Notice: Subject to any disclaimer, the term of this patent is extended or adjusted under 35 U.S.C. 154(b) by 748 days.

(21) Appl. No.: 14/823,419

(22) Filed: Aug. 11, 2015

(65) Prior Publication Data
US 2017/0042227 A1 Feb. 16, 2017

(51) Int. Cl.
*A24F 47/00* (2006.01)
*A61M 15/06* (2006.01)
(Continued)

(52) U.S. Cl.
CPC .......... *A24F 47/008* (2013.01); *A61M 15/06* (2013.01); *H05B 1/0202* (2013.01); *H05B 1/0244* (2013.01); *H05B 1/0297* (2013.01); *H05B 3/04* (2013.01); *H05B 3/44* (2013.01); *A61M 2205/8206* (2013.01); *H05B 2203/014* (2013.01); *H05B 2203/021* (2013.01); *H05B 2203/022* (2013.01)

(58) Field of Classification Search
None
See application file for complete search history.

(56) References Cited

U.S. PATENT DOCUMENTS 8,511,318 B2    8/2013  Hon
2011/0265806 A1*  11/2011  Alarcon ............... A24F 47/00
                                                131/273
(Continued)

FOREIGN PATENT DOCUMENTS

EA      019736       5/2014
EP      2878215 A1   6/2015
(Continued)

OTHER PUBLICATIONS

International Search Report corresponding to European patent application PCT/EP2016/068867 dated Nov. 16, 2016 and Written Opinion.

(Continued)

*Primary Examiner* — Phu H Nguyen
(74) *Attorney, Agent, or Firm* — Harness, Dickey & Pierce, P.L.C.

(57) ABSTRACT

A power supply section for an e-vaping device includes a sensor housed in a housing, a sensor holder holding the sensor, the sensor holder disposed in the housing to divide the housing into a first portion and a second portion, and the sensor and the sensor holder configured to substantially prevent air flow from the first portion into the second portion, and a power source disposed in the second portion. The construction of this unit insures that gases that may be produced by outgassing of the battery cell will be vented to the environment and that those gases will be isolated from the air that is mixed with the vaporized e-liquid and inhaled by the user.

17 Claims, 5 Drawing Sheets

(51) Int. Cl.
*H05B 1/02* (2006.01)
*H05B 3/04* (2006.01)
*H05B 3/44* (2006.01)

(56) References Cited

U.S. PATENT DOCUMENTS

| 2014/0020696 | A1* | 1/2014 | Liu | A24F 47/002 |
| | | | | 131/329 |
| 2014/0261495 | A1* | 9/2014 | Novak, III | A24F 47/008 |
| | | | | 131/329 |
| 2015/0114409 | A1 | 4/2015 | Brammer et al. | |

FOREIGN PATENT DOCUMENTS

| GB | 2518598 A | 4/2015 |
| RU | 122254 U1 | 11/2012 |
| WO | WO-2004/080216 A1 | 9/2004 |
| WO | WO-2011160788 A1 | 12/2011 |
| WO | WO-2013171206 A1 | 11/2013 |
| WO | WO-2014110119 A1 | 7/2014 |
| WO | WO-2014150704 A2 | 9/2014 |

OTHER PUBLICATIONS

Russian Decision to Grant for corresponding Application No. 2018108188, dated Aug. 30, 2019, English translation thereof.

* cited by examiner

POWER SUPPLY SECTION CONFIGURATION FOR AN ELECTRONIC VAPING DEVICE AND ELECTRONIC VAPING DEVICE

BACKGROUND OF THE INVENTION

Field of the Invention

Some example embodiments relate generally to a power supply section configuration for an electronic vaping device, and/or an electronic vaping device.

Related Art

Electronic vaping devices are used to vaporize a liquid material into a vapor in order for an adult vaper to inhale the vapor. These electronic vaping devices may be referred to as e-vaping devices. An e-vaping device may typically include several e-vaping elements such as a power supply section and a cartomizer. The power supply section includes a power source such as a battery, and the cartomizer includes a heater along with a reservoir capable of holding the liquid material. The cartomizer typically includes the heater which is in contact with a liquid material via a wick, the heater being configured to heat the liquid material to produce a vapor. The liquid material typically includes an amount of nicotine. An e-vaping device may also include a puff sensor that triggers heating of the liquid material when the user puffs on the e-vaping device in order to produce the vapor inhaled by the adult vaper.

Conventional e-vaping devices include the puff sensor at a distal end of the device in the power supply section, which is typically at an opposite end of the device from the mouthpiece. Accordingly, during use, air enters at the tip of the device and circulates around the power source and then passes through the cartomizer. The air is then mixed with the vaporized liquid and is inhaled by the adult vaper. The power source may be a lithium ion battery cell which may exhibit outgassing during operation resulting in a potentially harmful gas being released from the battery cell. Because the incoming air must flow over the power source the result may be a mixing of the battery cell outgas with the vaporized Liquid inhaled by the adult vaper. In addition, after constant use the vent hole at the tip may eventually be clogged as a result of dust or other environmental conditions and the resistance to draw (RTD) may be increased which may result in a decreased life for the battery.

SUMMARY OF THE INVENTION

At least one example embodiment relates to a power supply section of an e-vaping device.

In one example embodiment, the power supply section for an e-vaping device includes a sensor housed in a housing, a sensor holder holding the sensor, the sensor holder disposed in the housing to divide the housing into a first portion and a second portion, and the sensor and the sensor holder configured to substantially prevent air flow from the first portion into the second portion, and a power source disposed in the second portion. The sensor holder section as well as the power source section will each contain separate and independent vent holes respectively. The vent hole in the sensor section allows air to enter into the cartomizer as well as activates the sensor when in use. The vent hole in the power supply section allows the outgassing from the battery cell to exit through the tip of the e-vaping device. As a result of the separation of compartments between the sensor and power supply, the inhaled air may be substantially preventing from passing over the power supply. Thus, the inhaled vapor will not mix with the gases released from the battery cell. If outgassing occurs from the battery cell, the resulting gas may be released through the vent in the tip of the e-vaping device.

In one embodiment, the sensor holder holds the sensor such that the sensor senses a pressure drop in the first portion, the sensor may be a puff sensor and the power source may be a battery. The sensor holder is a hollow structure having a first dimension section and a second dimension section, the first dimension section defining a first cavity having a least a first dimension, the second dimension section defining a second cavity having a least a second dimension, the second cavity corresponding to a shape of the sensor, and the first dimension being smaller than the second dimension.

In one embodiment, the sensor holder has a substantially cylindrical shape, and the first and second dimensions are first and second diameters, respectively. The sensor holder may have an annular flange at a transition between the first dimension section and the second dimension section.

In one embodiment, the sensor holder includes at least one first projection projecting from one end of the sensor holder, the at least one first projection being between the sensor holder and the power source, and the power supply section includes at least one second projection projecting from another end of the sensor holder.

In one embodiment, the sensor includes a control circuitry configured to control supply of power from the power source.

Alternatively, the power supply circuit includes a control circuitry that is coupled with the sensor and configured to control supply of power from the power source.

Example embodiments relate to a power supply section for an e-vaping device that includes a seal between a first portion and a second portion of the power supply section, the seal being configured to substantially prevent air flow from the first portion into the second portion, and a power source in the second portion.

In one embodiment, the seal includes a sensor and a sensor holder, the sensor being electrically coupled to the power source.

At least one example embodiment relates to an e-vaping device.

In one embodiment, the e-vaping device includes a cartomizer including a liquid reservoir holding a liquid, a mouthpiece and a heater configured to heat the liquid, and a power supply section removably connected to the cartomizer via a connector and including a sensor housed in a housing, a sensor holder holding the sensor, the sensor holder disposed in the housing to divide the housing into a first portion and a second portion, and the sensor and the sensor holder are configured to substantially prevent air flow from the first portion into the second portion, and a power source disposed in the second portion and configured to supply power to the heater.

BRIEF DESCRIPTION OF THE DRAWINGS

The above and other features and advantages of example embodiments will become more apparent by describing in detail, example embodiments with reference to the attached drawings. The accompanying drawings are intended to depict example embodiments and should not be interpreted

DETAILED DESCRIPTION

Figure 1A:
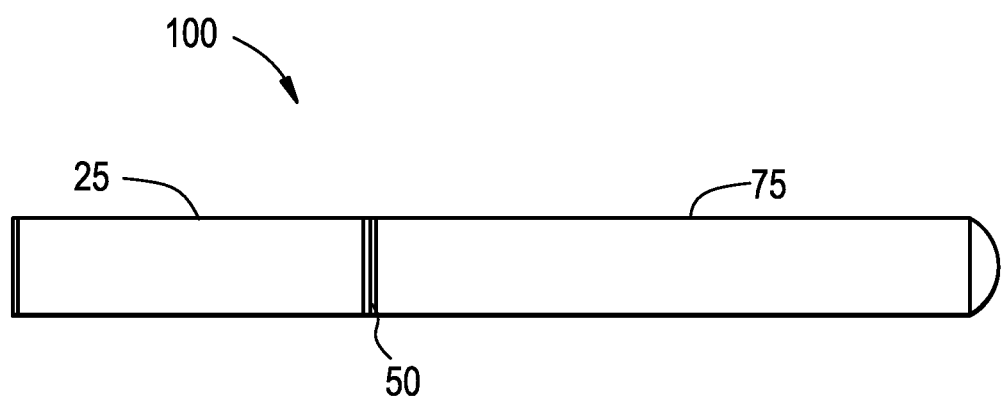
FIGS. 1A-1B are illustrations of an e-vaping device according to at least one example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Figure 1B:
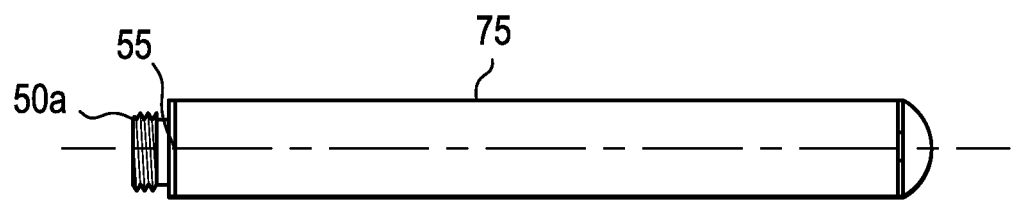

FIGS. 1A-1B illustrate an e-vaping device according to at least one example embodiment. In FIG. 1A, the e-vaping device 100 includes a replaceable cartomizer (or first section) 25 and a power source section (or second section) 75, which are coupled together at a connector 50. Both the power source section 75 and the cartomizer 25 are illustrated as having a cylindrical shape of substantially equal diameter. However, it will be appreciated that example embodiments are not limited to a cylindrical shape. For example, the power source section 75 and the cartomizer 25 may have a rectangular or other shape. In one example embodiment, a power source or battery and control circuitry are included in the power source section 75. Upon completing the connection between the power source section 75 and the cartomizer 25 at the connector 50, when an adult vaper uses the e-vaping device 100, the power source included in the power source section 75 is electrically connected with a heater element of the cartomizer 25. It should be noted that although FIG. 1A illustrates the e-vaping device 100 having two releasably coupled sections 25 and 75, example embodiments may include a unitary e-vaping device where the above-discussed features are housed in a single section.

In FIG. 1B, the power source section 75 includes a male connector 50*a* of the connector 50 located at an end thereof. Although a male connector 50*a* is illustrated in FIG. 1B, the connector 50*a* may instead be a female connector. The power source section 75 may also include an air vent 55 configured to let air flow therein during use of the e-vaping device by an adult vaper.

Figure 2:
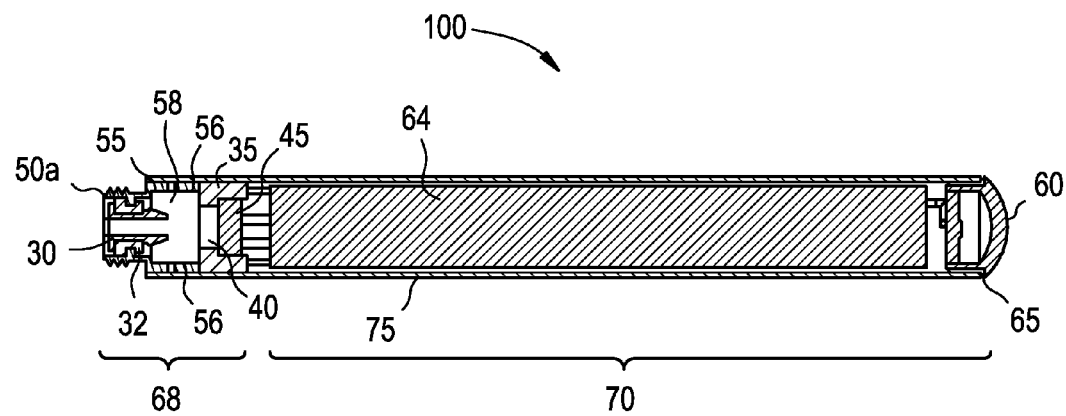
FIG. 2 is a longitudinal cross-section of a power supply section for an e-vaping device, according to at least one example embodiment.

FIG. 2 illustrates a cross-section of a power source section for an e-vaping device, according to at least one example embodiment. As shown, a puff sensor holder 35 divides the power source section 75 into a sensing portion 68 and a power source portion 70. The power source portion 70 includes a power source 64. The power source 64 may be, for example, a battery. The power source portion 70 also includes a heater activation light or LED 60 configured to glow when power is generated. In one embodiment, the heater activation light 60 is at a proximate end of the power source section 75 so that the heater activation light 60 takes on the appearance of a burning coal during a puff. In one embodiment, the proximate end of the power source section 75 may also include at least one air vent 65 configured to evacuate any gases present in the power source section 75.

In one embodiment, the sensing portion 68 includes a chamber 58 configured to receive air via the air vents 55 when the e-vaping device is in use. In an embodiment, the air vents 55 are provided at an angle with respect to a longitudinal direction of the power source section 75. For example, an acute angle ensures greater efficiency in allowing the airflow to enter the chamber 58 during use of the e-vaping device 100. The puff sensor holder 35 holds or supports a puff sensor 40 such that the puff sensor 40 may sense when an adult vaper is using the e-vaping device 100, for example, sensing the receipt of air through the air vents 55 and the chamber 58, or sensing a pressure drop in the chamber 58 when in use.

In one embodiment, the sensing portion 68 may also include control circuitry 45 that may be integrated with or connected to the puff sensor 40 to control the supply of power in response to the puff sensor 40 sensing that an adult vaper is using the e-vaping device. The control circuitry 45 may be connected to the heater activation light or LED 60 of the power source portion 70 and a heater in the cartomizer 25 when the cartomizer 25 is connected to the power source section 75.

According to at least one example embodiment, the puff sensor 40 is placed in close proximity to the male connector 50a and is held in place via the puff sensor holder 35. The male connector 50a may include a suction post 30 configured to allow a path for air entering air vents 55, during use of the e-vaping device, to flow to the cartomizer 25. The suction post 30 may be a tubular section at an end of the power source section 75 and is configured to ensure a direct air path between the chamber 58 and the cartomizer 25 when the power source section 75 is connected to the cartomizer 25. The suction post 30 may be held in place via a gasket ring 32.

In one embodiment, the puff sensor holder 35 is held in place and/or substantially prevented from moving inside the sensing portion 68 by one or more projections 56 located against an inside wall of the power source section 75. Alternatively, the projections 56 may be a thicker portion of the inside wall of the power source section 75. Accordingly, the puff sensor holder 35 is substantially prevented from sliding towards the male connector 50a by the projections 56.

During operation of the e-vaping device, the puff sensor 40 is configured to sense an air pressure drop in the chamber 58 and to initiate the application of voltage from the power source via the control circuitry 45.

In one embodiment, the combination of the puff sensor holder 35 and the puff sensor 40 form a seal configured to substantially hermetically isolate the power source portion 70 from the sensing portion 68. Accordingly, when airflow is created in the sensing portion 68 as a result of using the e-vaping device 100 by an adult vaper, which draws outside air from the air vents 55 and create a pressure drop at the puff sensor 40, little or no airflow enters the power source portion 70 by the puff sensor holder 35. As a result, degradation of the power supply source 64 due to contact with the airflow is reduced or substantially prevented. In addition, outgassing from the power source 64 is substantially prevented from entering into the cartomizer 25 via the sensor chamber 58. Outgassing from the power source 64 will be via vent hole 65.

Figure 3A:
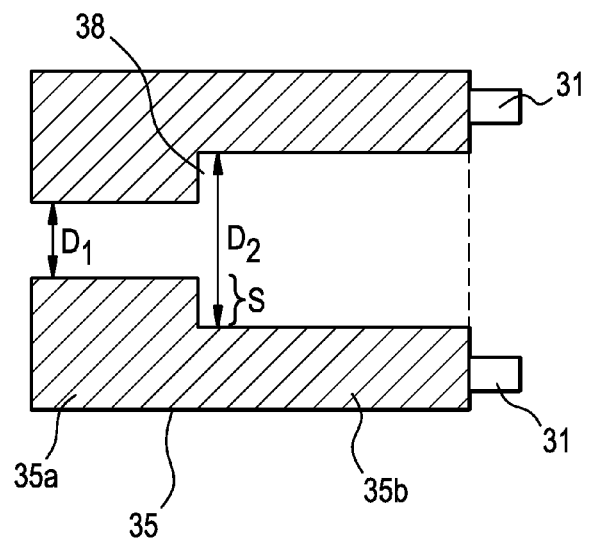
FIGS. 3A-3E are illustrations of a puff sensor and a puff sensor holder, according to at least one example embodiment.

FIG. 3A is a cross-section of a puff sensor holder, according to at least one example embodiment. In FIG. 3A, the puff sensor holder 35 is a hollow cylinder having a first diameter section 35a and a second diameter section 35b. The first diameter section 35a has a first inner diameter D1 and defines a first cavity, and the second diameter section 35b has a second inner diameter D2 and defines a second cavity. In example embodiments, D1 is less than D2 such that an inner annular flange 38 is formed in the puff sensor holder 35. The space defined by the second inner diameter D2 matches the shape of the puff sensor 40 such that the puff sensor 40 can be snuggly and substantially hermetically seated in the puff sensor holder 35.

In one embodiment, projections 31 are at an end of the second diameter section 35b. It should be noted that, the puff sensor 40 is not limited to having, for example, a circular cross-section, and accordingly, the cross-section of the interior space of the second diameter section 35b is not limited to a circular cross-section.

The first and second diameter sections 35a and 35b have the same outer diameter, which closely matches the inner diameter of the housing for the power source section 75 such that the puff sensor holder 35 is substantially hermetically seated in the power source section 75. The combination of the puff sensor 40 and the puff sensor holder 35 forms a seal that substantially hermetically isolates the sensing portion 68 from the power source portion 70. In one embodiment, the puff sensor holder 35 may include polydimethyisiloxane (PDMS) or silicone.

In one embodiment, the projections 31 provide a physical separation between the puff sensor holder 35 and a battery 64 housed in the power source portion 70. Accordingly, the projections 31 are configured to, for example, prevent the battery 64 from contacting the puff sensor holder 35, preventing potential short of battery connection with control circuitry contacts, or to substantially prevent either or both of the puff sensor holder 35 and the battery 64 from moving.

Figure 3B:
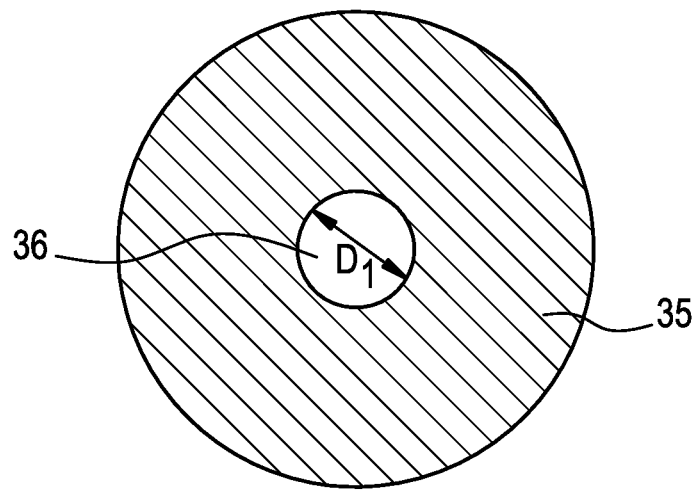
Figure 3C:
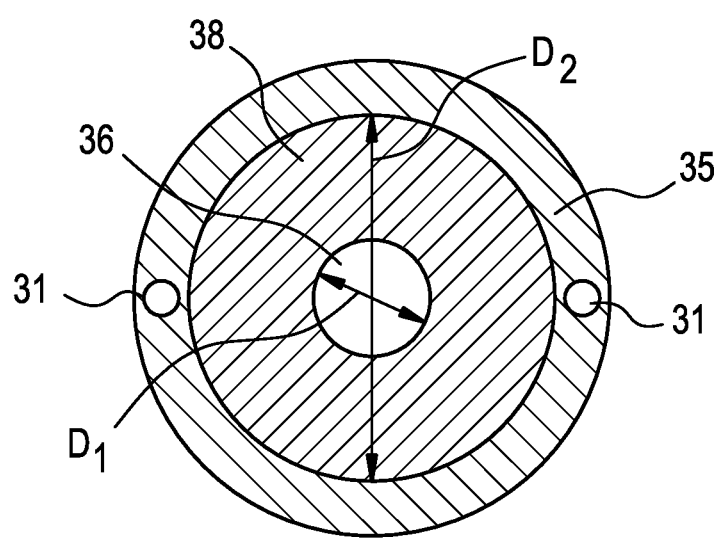

FIG. 3B is an end view of the puff sensor holder 35 at the end of the first diameter section 35a in FIG. 3A. In FIG. 3B, the puff sensor holder 35 includes a circular opening 36 having diameter D1. It should be noted that the opening 36 may have a shape other than circular. For example, the opening 36 may have a square or a rectangular shape, among other shapes. FIG. 3C is an end view of the puff sensor holder 35 of the second diameter section 35b in FIG. 3A. FIG. 3C illustrates annular flange 38 upon which the puff sensor 40 seats.

Figure 3D:
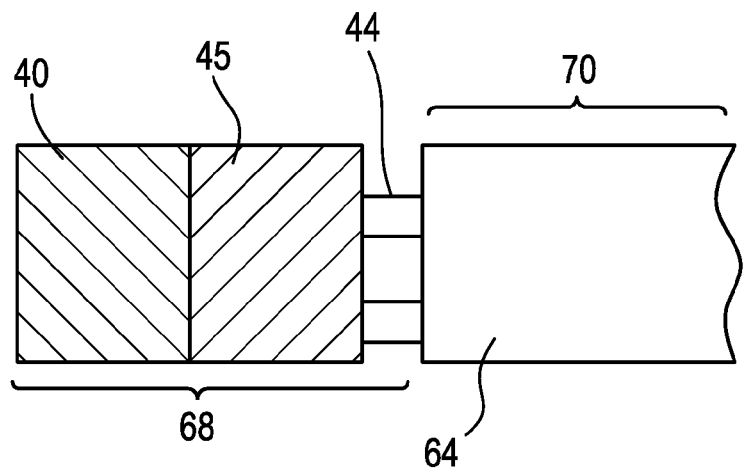

FIG. 3D is a longitudinal cross-section of a puff sensor 40, according to at least one example embodiment. In one embodiment, the puff sensor 40 is coupled to the control circuitry 45. The control circuitry 45 is configured to control the flow of power (e.g., current) from the battery 64. In one embodiment, the control circuitry 45 includes electrodes 44 and a processor configured to control the application of power from the battery 64 when an air pressure drop in the chamber 58 (illustrated in FIG. 2) is sensed by the puff sensor 40 due to the use of the e-vaping device by an adult vaper. Although the control circuitry 45 is illustrated as having a cylindrical shape concentric with the shape of the puff sensor 40, the control circuitry 45 may have other shapes and may include one or more additional control components configured to control the application of power from the battery 64.

Figure 3E:
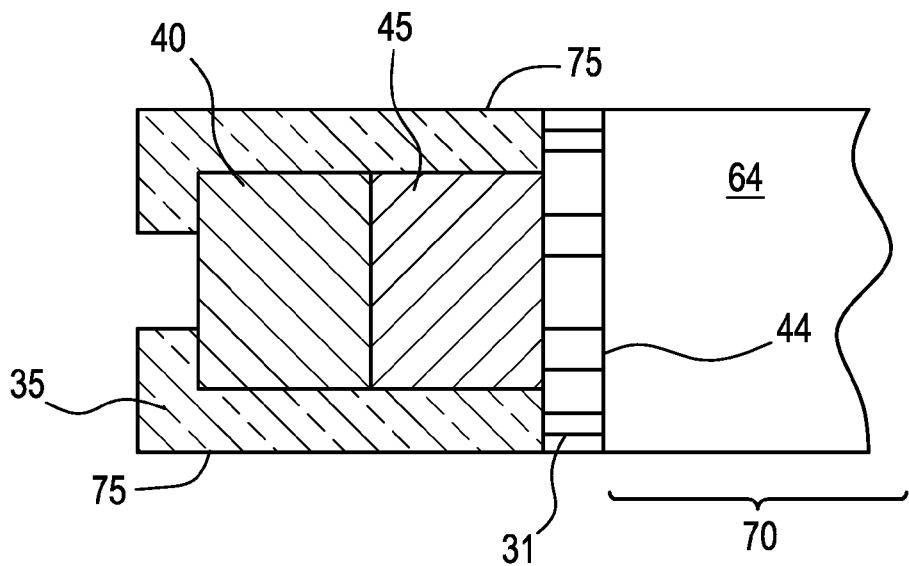

FIG. 3E is a longitudinal cross-sectional view of a puff sensor being held in a puff sensor holder, according to at least one example embodiment. In FIG. 3E, the puff sensor 40 is snuggly seated within the puff sensor holder 35. In one embodiment, the puff sensor holder 35 is snuggly fit against an inside wall of the power source section 75. For example, the cylindrical puff sensor holder 35 is substantially hermetically secured against the inside cylindrical walls of the power source section 75. In one embodiment, the puff sensor 40 abutts against the flange 38 of the puff sensor holder 35. The flange 38 may be configured to snuggly seat the puff sensor 40 within the puff sensor holder 35. At an opposite end of the puff sensor 40 from the flange 38 in a longitudinal direction of the puff sensor 40, the electrodes 44 are configured to ensure electrical and control coupling with the battery 64 housed in the power source portion 70. Accordingly, in operation, when an adult vaper uses the e-vaping device, the control circuitry 45 is configured to supply power in response to the puff sensor 40 sensing that an adult vaper is drawing on the e-vaping device. In one embodiment, the projections 31, located at an opposite side of the puff sensor holder 35 from the opening 36 in a longitudinal direction of the puff sensor holder 35, are configured to substantially prevent the battery 64 from contacting the puff sensor holder 35 and/or to substantially prevent either or both of the puff sensor holder 35 and the battery 64 from moving.

In view of the above description illustrated in FIGS. 3A-3E, during use of the e-vaping device, air that penetrates through the vents 55 and that circulates at the puff sensor 40 is substantially prevented from entering the power source portion 70 by the puff sensor holder 35. As a result, degradation of the battery 64 housed in the power source portion 70 can be substantially prevented or reduced. In addition, outgassing from the power source 64 is substantially prevented from entering into the cartomizer 25 via the sensor chamber 58. Outgassing from the power source 64 will be via vent hole 65.

Figure 4:
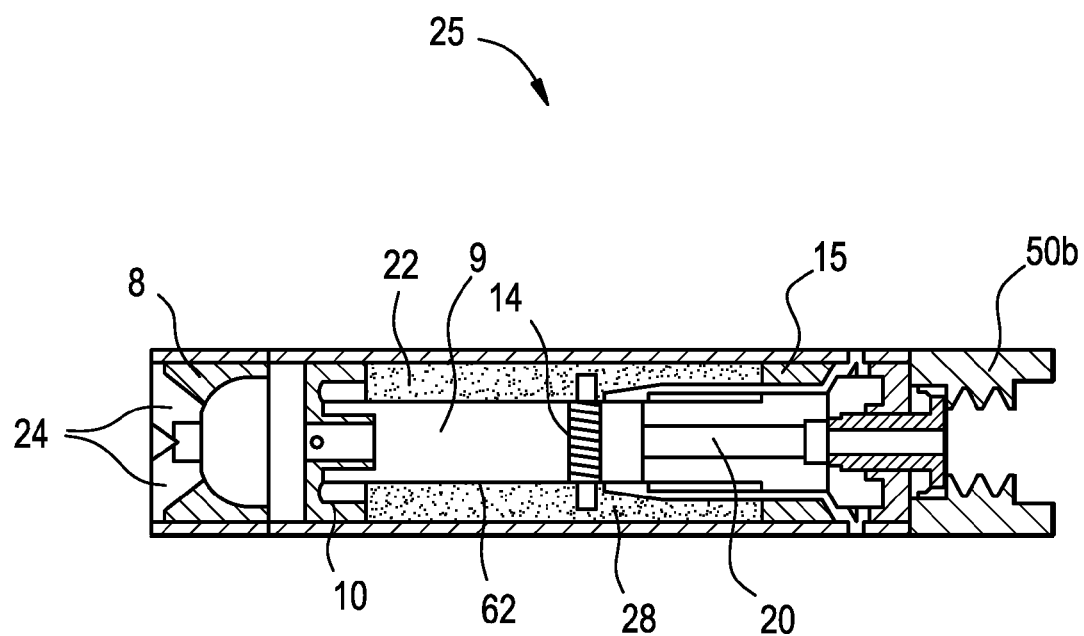
FIG. 4 is a cross-sectional view of cartomizer according to at least one example embodiment.

FIG. 4 is a cross-sectional view of cartomizer according to at least one example embodiment. In FIG. 4, the replaceable cartomizer 25 may include a liquid supply reservoir 22 including a liquid, a wick 28 configured to wick the liquid from the liquid supply reservoir 22, and a heater element 14 configured to heat the liquid in the wick 28 to form a vapor. In an example embodiment, the heater 14 is contained in the cartomizer 25 downstream of, and in spaced apart relation to, the portion of central air passage 20 defined by a seal 15. When an adult vaper uses the e-vaping device, the air flows from vents 55 and the suction post 30 of the power source section 75 into the bore of the central air passage 20 and into the outer air passage 9. According to example embodiment, the heater 14 can be in the form of a wire coil, a planar body, a ceramic body, a single wire, a cage of resistive wire or any other suitable form. The wick 28 may be in communication with both the liquid material in the liquid supply reservoir 22 and with the heater 14, such that the wick 28 provides a path for the liquid material to flow between the liquid supply reservoir 22 and the heater 14. The wick 28 may be constructed of a fibrous and flexible material, and/or may include at least one filament having a capacity to draw a liquid. In one example embodiment, the power supply 64 included in the power source section 75 may be operably connected by the control circuitry 45 to the heater 14 to apply a voltage across the heater 14 in order to heat the liquid and generate a vapor. The cartomizer 25 and the power source section 75 are coupled together physically and electrically at threaded connections 50a and 50b, where 50a is a male threaded connection on the power source section 75 (see FIG. 2), and 50b is a female threaded connection on the cartomizer 25 (see FIG. 4).

In one example embodiment, a ground (negative) connection may be formed via an electrical connection between the threaded connections 50a and 50b, and a (positive) voltage connection may be formed via the electrical connection between the post 30 of the power source section 75 and a post (not shown) of the cartomizer 25. For example, lead wires may connect the post 30 of the power source section 75 and the threaded connector 50a to control circuitry (not shown) in the power source section 75, and other lead wires may connect the threaded connector 50b and a post of the cartomizer 25 to the heater element 14. Accordingly, in operation, when the cartomizer 25 and the power source section 75 are coupled, a circuit is formed.

According to at least one example embodiment, the cartomizer 25 further includes a mouth-end insert 8 having at least one or two off-axis, diverging outlets 24. The mouth-end insert 8 may be in fluid communication with the central air passage 20 via the interior of inner tube 62, which extends through the stopper 10. Moreover, the heater 14 extends in a direction transverse to the longitudinal direction and heats the liquid material to a temperature sufficient to vaporize the liquid material and form a vapor. In other example embodiments, other orientations of the heater 14 may be contemplated. For example, the heater 14 and the heated portion of the wick 28 may be arranged longitudinally within the inner tube 62. The heater 14 may also be arranged centrally within the inner tube 62. However, in other example embodiments, the heater 14 may be arranged adjacent an inner surface of the inner tube 62.

In at least one example embodiment, the wick 28, liquid supply reservoir 22 and mouth-end insert 8 are contained in the cartomizer 25, and the power supply 64 is contained in the power source section 75.

Example embodiments having thus been described, it will be obvious that the same may be varied in many ways. Such variations are not to be regarded as a departure from the intended spirit and scope of example embodiments, and all modifications as would be obvious to one skilled in the art are intended to be included within the scope of the following claims.

What is claimed is:

1. A power supply section for an e-vaping device, comprising:
   a sensor housed in a housing;
   a sensor holder holding the sensor, the sensor holder dividing the housing into a first portion and a second portion, and the sensor together with the sensor holder being configured to prevent air flow between the first portion and the second portion, wherein the sensor and the sensor holder are each individually incapable of preventing the air flow between the first portion and the second portion; and
   a power source in the second portion.

2. The power supply section of claim 1, wherein the sensor holder holds the sensor such that the sensor senses a pressure drop in the first portion.

3. The power supply section of claim 2, wherein the sensor is a puff sensor.

4. The power supply section of claim 1, wherein the power source comprises a battery.

5. The power supply section of claim 1, further comprising:
    at least one air inlet in fluid communication with the first portion.

6. The power supply section of claim 1, wherein the sensor holder is a hollow structure having a first section and a second section, the first section defining a first cavity having a least a first radial dimension, the second section defining a second cavity having a least a second radial dimension, the second cavity corresponding to a shape of the sensor, and the first radial dimension being smaller than the second radial dimension.

7. The power supply section of claim 6, wherein
    the sensor holder has a substantially cylindrical shape; and
    the first and second radial dimensions are first and second diameters, respectively.

8. The power supply section of claim 7, wherein the sensor holder has an annular flange at a transition between the first section and the second section, the sensor being seated on the annular flange.

9. The power supply section of claim 1, wherein the sensor holder comprises at least one first projection projecting from one end of the sensor holder, the at least one first projection being between the sensor holder and the power source.

10. The power supply section of claim 1, wherein the power supply section comprises at least one second projection at another end of the sensor holder, the sensor holder being seated on the second projections.

11. The power supply section of claim 1, wherein the sensor comprises control circuitry configured to control supply of power from the power source.

12. The power supply section of claim 1, further comprising:
    control circuitry coupled with the sensor and configured to control supply of power from the power source.

13. The power supply section of claim 1, further comprising:
    an LED cap at a distal end of the second portion.

14. The power supply section of claim 13, wherein the LED cap includes a vent configured to allow outgassing from the power supply section to be released.

15. An e-vaping device, comprising:
    a cartridge including a liquid reservoir holding a liquid, a mouthpiece and a heater configured to heat the liquid; and
    a power supply section removably connected to the cartridge via a connector and including,
        a sensor housed in a housing,
        a sensor holder holding the sensor, the sensor holder dividing the housing into a first portion and a second portion, and the sensor together with the sensor holder being configured to prevent air flow between the first portion and the second portion, wherein the sensor and the sensor holder are each individually incapable of preventing the air flow between the first portion and the second portion, and
        a power source in the second portion and configured to supply power to the heater.

16. A power supply section for an e-vaping device, comprising:
    a sensor and a sensor holder between a first portion and a second portion of the power supply section, the sensor together with the sensor holder being configured to prevent air flow between the first portion and the second portion, wherein the sensor and the sensor holder are each individually incapable of preventing the air flow between the first portion and the second portion; and
    a power source in the second portion.

17. The power supply section of claim 16, wherein the sensor is electrically coupled to the power source.

* * * * *